(12) United States Patent
Carter et al.

(10) Patent No.: US 7,943,147 B2
(45) Date of Patent: May 17, 2011

(54) DSRNAS AS INFLUENZA VIRUS VACCINE ADJUVANTS OR IMMUNO-STIMULANTS

(75) Inventors: William A. Carter, Spring City, PA (US); David Strayer, Bryn Mawr, PA (US)

(73) Assignee: Hemispherx Biopharma, Philadelphia, PA (US)

( * ) Notice: Subject to any disclaimer, the term of this patent is extended or adjusted under 35 U.S.C. 154(b) by 0 days.

(21) Appl. No.: 11/634,389

(22) Filed: Dec. 6, 2006

(65) Prior Publication Data

US 2007/0224219 A1    Sep. 27, 2007

Related U.S. Application Data

(60) Provisional application No. 60/793,239, filed on Apr. 20, 2006, provisional application No. 60/752,898, filed on Dec. 23, 2005, provisional application No. 60/742,906, filed on Dec. 7, 2005.

(51) Int. Cl.
*A61K 49/00* (2006.01)
*A61K 39/00* (2006.01)
*A61K 39/145* (2006.01)
*A61K 45/00* (2006.01)
*A61K 48/00* (2006.01)
*A61K 39/285* (2006.01)

(52) U.S. Cl. ............... 424/209.1; 424/206.1; 424/184.1; 424/9.1; 424/280.1; 514/44

(58) Field of Classification Search ........................ None
See application file for complete search history.

(56) References Cited

U.S. PATENT DOCUMENTS

| | | | |
|---|---|---|---|
| 3,906,092 A | 9/1975 | Hilleman et al. | |
| 4,349,538 A | 9/1982 | Levy | |
| 6,589,529 B1 * | 7/2003 | Choi et al. | 424/186.1 |
| 2006/0223742 A1 * | 10/2006 | Salazar | 514/7 |

FOREIGN PATENT DOCUMENTS

| WO | WO 91/18611 | * 12/1991 |
|---|---|---|
| WO | WO 2005/014038 A1 | 2/2005 |
| WO | 2008/109083 | 9/2008 |

OTHER PUBLICATIONS

Ichinohe et al., Synthetic Double-Stranded RNA Poly (I:C) Combined with Mucosal Vaccine Protects against Influenza Virus Infection, 2005, Journal of Virology, vol. 79, No. 5, pp. 2910-2919.*
Cinatl et al., The threat of avian influenza A (H5N1). Part IV: development of vaccines, 2007, Medical Microbiology and Immunology, vol. 196, pp. 213-225.*
Associated Press, AIDS Vaccine Fails, so Merck Is Ending Study, Saturday, Sep. 22, 2007, Washingtonpost.com.*
Philadelphia-Business Wire, Ampligen® Enhances the Effectiveness of Tamiflu Against Avian Influenza; Second Independent Preclinical Study Confirms dsRNA Increases Flu Vaccine Effectiveness, Sep. 6, 2005.*
Cooper et al., Safety and immunogenicity of CPG 7909 injection as an adjuvant to Fluarix influenza vaccine, 2004, Vaccine, vol. 22, pp. 3136-3143.*
ADIS R&D Report, Mismatched Double-Stranded RNA:PolyI:PolyC12U, 2004, Drugs in R&D, vol. 5, No. 5, pp. 297-304.*
Richman et al., The Challenge of Finding a Cure for HIV Infection, 2009, Science, vol. 323, pp. 1304-1307.*
Sanofi-Pasteur Influenza Virus Vaccine, H5N1 package insert, Apr. 2007.*
Padalko et al., The Interferon Inducer Ampligen [Poly(I)-Poly(C12U)] Markedly Protects Mice against Coxsackie B3 Virus-Induced Myocarditis, 2004, Antimicrobial Agents and Chemotherapy, vol. 48, No. 1, pp. 267-274.*
Hubbell et al., Independent Sensitivity of Human Tumor Cell Lines to Interferon and Double-Stranded RNA, 1984, Cancer Research, vol. 44, pp. 3252-3257.*
Business wire, Business Publications: Ampligen® Enhances the Effectiveness of Tamiflu Against Avian Influenza; Second Independent Preclinical Study Confirms dsRNA Increases Flu Vaccine Effectiveness, Sep. 6, 2005, accessed Online on Dec. 16, 2010 <<http://findarticles.com/p/articles/mi_m0EIN/is_2005_Sept_6/ai_n15343872/>>.*
Tamura et al. "Cross-protection against influenza virus infection afforded by trivalent inactivated vaccines inoculated intranasally with cholera toxin B subunit" J. Immunol. 149:981-988 (1992).
International Search Report mailed Oct. 17, 2007 for Int'l Appln. No. PCT/US2006/46356.
Written Opinion mailed Oct. 17, 2007 for Int'l Appln. No. PCT/US2006/46356.
Brodsky et al. "Clinical studies with Ampligen (mismatched double-stranded RNA)" *Journal of Biological Response Modifiers*, vol. 4, No. 6, pp. 669-675 (Dec. 1985).
Trumpfheller et al. "The microbial mimic poly IC induces durable and protective CD4+ T cell immunity together with a dendritic cell targeted vaccine" *Proceedings of the National Academy of Sciences USA*, vol. 105, No. 7, pp. 2574-2579 (Feb. 2008).
U.S. Food and Drug Administration, Bethesda, Maryland, *FDA Pandemic Influenza Preparedness Strategic Plan* http://www.fda.gov/oc/op/pandemic/strategicplanupdate03_08.html (Mar. 2008).
Supplementary European Search Report dated Feb. 22, 2010 and European Search Opinion issued in connection with EP 06844824.0.
Fujimoto et al, "Polyriboinosinic polyribocytidylic acid [poly(I:C)]/TLR3 signaling allows class I processing of exogenous protein and induction of HIV-specific CD8+ cytotoxic T lymphocytes", International Immunology 16(1):55-63 (2004).
Adar et al. "A universal epitope based influenza vaccine and its efficacy against H5N1" Vaccine 27:2099-2107 (2009).
Anonymous "Guidance for Industry: Animal models—Essential elements to address efficacy under the animal rule" U.S. Dept. of Health and Human Services, pp. 4-19 (2009).

(Continued)

*Primary Examiner* — Zachariah Lucas
*Assistant Examiner* — Benjamin P Blumel
(74) *Attorney, Agent, or Firm* — Nixon & Vanderhye, P.C.

(57) ABSTRACT

Vaccine protection against acute or chronic viral infection is facilitated by using as an adjuvant or immuno-stimulant, a dsRNA together with an anti-influenza vaccine.

4 Claims, 5 Drawing Sheets

OTHER PUBLICATIONS

Avril et al. "Not all polyriboinosinic-polyribocytidylic acids (poly I:C) are equivalent for inducing maturation of dendritic cells implication for α-type-1 polarized DCs" J. Immunother. 32:353-362 (2009).

Crawford "New drug and biological drug products; evidence needed to demonstrate effectiveness of new drugs when human efficacy studies are not ethical or feasible" Federal Register 67:37988-37998 (2002).

Flulaval—Influenza virus vaccine—Suspension for intramuscular injection 2009-2009 formula http://www.pdr.net/druginformation/documentretrievalprinterfriendlyn_local.aspx, pp. 1-9 (2009).

Flumist Rx—Influenza virus vaccine live, intranasal spray http://www.pdr.net/druginformationdocumentretrievalprinterfrindlyn_local.aspx, pp. 1-14 (2009).

Furuse et al. "Evolution of the M gene of the influenza A virus in different host species: Large-scale sequence analysis" Virology J. 6:67 (2009).

Hasegawa et al. "Development of mucosal adjuvants for intranasal vaccine for H5N1 influenza viruses" Therap. Clin. Risk Manag. 5:125-132 (2009).

Ichinohe et al. "Cross-protection against H5N1 influenza virus infection is afforded by intranasal inoculation with seasonal trivalent inactivated influenza vaccine" J. Infect. Dis. 196:1313-1320 (2007).

Shuren "Draft guidance for industry on animal models—Essential elements to address efficacy under the animal rule" Federal Register 74:3610-3611 (2009).

Stahl-Hennig et al. "Synthetic double-stranded RNAs are adjuvants for the induction of T helper 1 and humoral immune responses to human papillomavirus in rhesus macaques" PLOS Pathogens 5:1-15 (2009).

Sui et al. "Structural and functional bases for broad-spectrum neutralization of avian and human influenza A viruses" Nature Struc. Mol. Biol. 16:265-273 (2009).

Tamura et al. "Mechanisms of broad cross-protection provided by influenza virus infection and their application to vaccines" Jpn. J. Infect. Dis. 58:195-207 (2005).

Wang & Palese "Universal epitopes of influenza virus hemagglutinins?" Nature Struc. Mol. Biol. 16:233-234 (2009).

Wang et al. "Monoclonal antibody recognizing SLLEVET epitope of M2 protein potently inhibited the replication of Influenza A viruses in MDCK cells" Biochem. Biophys. Res. Comm. 385:118-122 (2009).

Yuki & Kiyono "New generation of mucosal adjuvants for the induction of protective immunity" Rev. Med. Virol. 13:293-310 (2003).

T. Ichinohe et al., "Synthetic Double-Stranded RNA Poly(I:C) Combined with Mucosal Vaccine Protects against Influenza Virus Infection", Journal of Virology, vol. 79, No. 5, pp. 2910-2919, Mar. 2005.

S. Tamura et al., "Cross-Protection Against Influenza Virus Infection Afforded by Trivalent Inactivated Vaccines Inoculated Intranasally with Cholera Toxin B Subunit", The Journal of Immunology, vol. 149, No. 3, pp. 981-988, Aug. 1, 1992.

H. Hasegawa et al., "Development of Mucosal Adjuvants for Intranasal Vaccine for H5N1 Influenza Viruses", Therapeutics and Clinical Risk Management 2009:5, pp. 125-132.

D. R. Black et al., "Studies on the Toxicity and Antiviral Activity of Various Polynucleotides", Antimicrobial Agents and Chemotherapy, vol. 3, No. 2, pp. 198-206, Feb. 1973.

W. E. Stewart, II et al., "Increased Susceptibility of Cells Treated with Interferon to the Toxicity of Polyriboinosinic Polyribocytidylic Acid", Proc. Nat. Acad. Sci. USA, vol. 69, No. 7, pp. 1851-1854, Jul. 1972.

T. Ichinohe et al., "Intranasal Administration of Adjuvant-Combined Vaccine Protects Monkeys From Challenge with the Highly Pathogenic Influenza A H5N1 Virus", Journal of Medical Virology 82, pp. 1754-1761, 2010.

* cited by examiner

FIGURE 2

DSRNAS AS INFLUENZA VIRUS VACCINE ADJUVANTS OR IMMUNO-STIMULANTS

CROSS REFERENCE TO RELATED APPLICATIONS

This application is a utility version of provisional application Ser. No. 60/793,239 filed Apr. 20, 2006, Ser. No. 60/752,898 filed Dec. 23, 2005 and Ser. No. 60/742,906 filed Dec. 7, 2005, the entire content of each of which is hereby incorporated by reference in this application Vaccine protection against acute or chronic viral infection is facilitated by using, together with an anti-influenza vaccine, as an adjuvant or immuno-stimulant, a dsRNA.

BACKGROUND OF THE INVENTION

Adjuvants have been used to facilitate vaccines in affording immunization to protect animals including humans. Identifying an efficient and effective adjuvant is often a difficult task.

Of particular interest are vaccines for protecting against influenza viruses, and of current interest avian influenza virus H5N1 (bird flu) including Vietnam and Hong Kong strains. Inactivated vaccines against influenza virus have been administered parenterally to induce serum antibodies and also to the nasal mucosa to provide mucosal immunity to influenza virus.

Several adjuvants are known such as alum, squalene emulsion (MF 59, Chiron Vaccines), and Freund's adjuvant. Recently a synthetic dsRNA polyriboinosinic polyribocytldylic acid or poly (I:C) has been proposed as an adjuvant or immuno-stimulant for inactivated influenza virus vaccine; see Ichinohe et al, Journal of Virology, March 2005, p. 2910-2919.

DESCRIPTION OF THE INVENTION

Disclosed are methods of facilitating vaccine protection against an acute or chronic viral infection comprising the coordinated administration to a subject requiring protection an immunity-inducing amount of an anti-influenza vaccine together with, as an adjuvant, a dsRNA. Also disclosed are methods of facilitating vaccine protection against an acute or chronic viral infection comprising administering to a subject requiring protection an immunity-inducing amount of an anti-influenza vaccine in combination with, as an adjuvant or immuno-stimulant, a dsRNA.

The invention includes methods of facilitating vaccine protection against an acute or chronic viral infection comprising administering substantially simultaneously or sequentially to a subject requiring protection an immunity-inducing amount of an anti-influenza vaccine together in admixture with, as an adjuvant or immuno-stimulant, a dsRNA.

This invention also includes methods of protecting animals, including humans, susceptible to avian influenza infections against viral-induced pathology secondary to both antigenic drift and shift (as evidenced by rearrangement of the viral particle structure) and genomic rearrangement as well.

The invention further includes methods of enhancing immunization against influenza viruses by coordinated administration of a vaccine to patients together or conjointly a synthetic, specifically configured, double-stranded ribonucleic acid (dsRNA). The dsRNA of choice is AMPLIGEN®, available from HEMISPHER$_X$ BIOPHARMA, 1617 JFK Boulevard, Philadelphia, Pa. USA., asynthetic, specifically configured, double-stranded ribonucleic acid (dsRNA) which retains the immunostimulatory and antiviral properties of other double-stranded RNA molecules (dsRNA) but exhibits greatly reduced toxicity. Like other dsRNAs, Ampligen® can stimulate host defense mechanisms including innate immunity. AMPLIGEN® has the ability to stimulate a variety of dsRNA-dependent intracellular antiviral defense mechanisms including the 2', 5'-oligoadenylate synthetase/RNase L and protein kinase enzyme pathways.

In the context of the present invention, what is meant by "coordinated" use is, independently, either (i) co-administration, i.e. substantially simultaneous or sequential administration of the vaccine and of the dsRNA, or (ii) the administration of a composition comprising the vaccine and the dsRNA in combination and in a mixture, in addition to optional pharmaceutically acceptable excipients and/or vehicles.

The mismatched dsRNA may be of the general formula $rI_n \cdot r(C_{12}U)_n$. In this and the other formulae that follow r = ribo. Other mismatched dsRNAs for use in the present invention are based on copolynucleotides selected from poly $(C_m, U)$ and poly $(C_mG)$ in which m is an integer having a value of from 4 to 29 and are mismatched analogs of complexes of polyriboinosinic and polyribocytidilic acids, formed by modifying $rI_n \cdot rC_n$ to incorporate unpaired bases (uracil or guanine) along the polyribocytidylate ($rC_m$) strand. Alternatively, the dsRNA may be derived from $r(I) \cdot r(C)$ dsRNA by modifying the ribosyl backbone of polyriboinosinic acid ($rI_n$), e.g., by including 2'-O-methyl ribosyl residues. The mismatched may be complexed with an RNA-stabilizing polymer such as lysine and/or cellulose. Of these mismatched analogs of $rI_n \cdot rC_n$, the preferred ones are of the general formula $rI_n \cdot r(C_{11-14},U)_n$. or $rI_n \cdot r(C_{29},G)_n$, and are described by Carter and Ts'o in U.S. Pat. Nos. 4,130,641 and 4,024,222, the disclosures of which are hereby incorporated by reference. The dsRNA's described therein generally are suitable for use according to the present invention.

Other examples of mismatched dsRNA for use in the invention include:

$r(I) \cdot r(C4,U)$ $r(I) \cdot r(C7,U)$ $r(I) \cdot r(C13,U)$ $r(I) \cdot r(C22,U)$ $r(I) \cdot r(C20,G)$ and $r(I) \cdot r(C_{p\cdot 23}, G_{>p})$.

Alternatively the dsRNA may be the matched form, thus polyadenylic acid complexed with polyuridylic acid (poly A·poly U) may also be used.

Another aspect of the invention is the treatment of acute and chronic viral infections susceptible to vaccine prophylaxis therapy, available now or in the future including, for example, HIV, severe acute respiratory syndrome (SARS) and influenza including avian influenza employing a synergistic combination of an appropriate vaccine and a dsRNA.

BRIEF DESCRIPTION OF THE DRAWINGS

The invention is further explained and illustrated in the following examples and figures in which:

FIG. 2 is a table showing the results of Example 2;

The terms used in the Figures that follow are:

A/VN avian influenza/Vietnam (H5N1) strain
VN1194 avian influenza/Vietnam (H5N1) strain
05/06 Vaccine trivalent "seasonal" influenza vaccine for the 2005-2006 season
Amp AMPLIGEN®
I.N. intranasal
S.C. subcutaneous
Anti-A/VN IgA IgA antibodies raised against the avian influenza Vietnam strain
Anti-A/VN IgG IgG antibodies raised against the avian influenza Vietnam strain
A/VN virus titer quantitation of the amount of avian influenza virus Vietnam strain (i.e. as detected in nasal mucosal washings)
Anti-05/06 Vaccine antibodies raised against the 2005/2006 trivalent seasonal influenza vaccine
H5N1 avian influenza virus classification type

DESCRIPTION OF THE PREFERRED EMBODIMENTS

Example 1

Cross Protection Between Avian Influenza Strains

Figure 1:
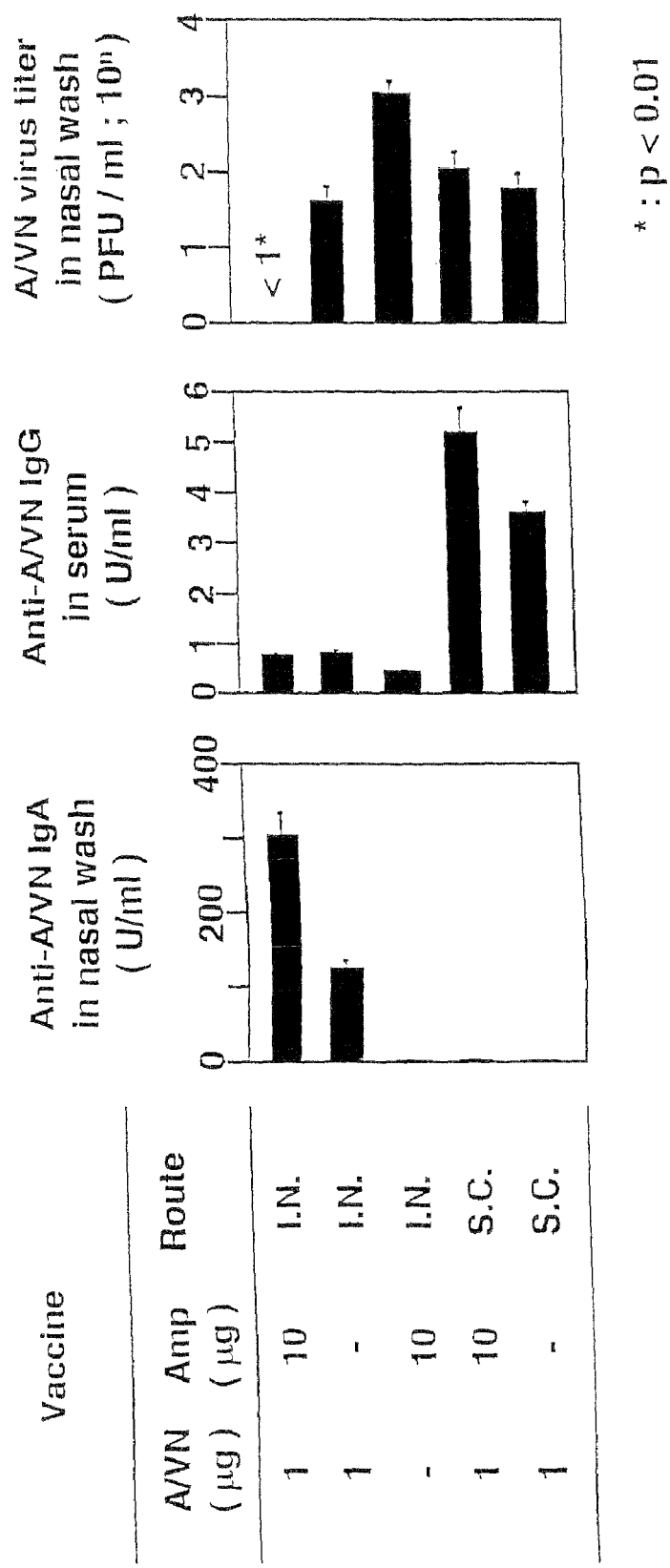
FIG. 1 is a table showing the results of Example 1.

This study was conducted in mice in the manner of Ichinohe et al, Journal of Virology, March, 2005, pages 2910-2919, this time using two different strains of avian flu virus, Vietnam and Hong Kong, and the dsRNA AMPLIGEN®, as described above, in combination or alone with the vaccine. The results are given in FIGS. 1 and 2.

In the first panel, from the antibodies detected in the nasal wash use of the (A/VN) vaccine by itself when administered intranasally provided a positive result in raising antibody but when administered with AMPLIGEN® produced a result that was more than twice than that of the vaccine used alone. No IgA antibodies were detected using AMPLIGEN® alone. The subcutaneous route did not yield any IgA antibodies in the nasal mucosa.

In contrast to this, a limited number of IgG antibodies were raised in the blood serum following intranasal administration but significantly greater amounts were obtained in the blood serum from the subcutaneous administration. Again, the combination of the vaccine plus AMPLIGEN® produced a greater result than with the vaccine alone.

The animals were then subjected to a challenge to avian influenza virus Vietnamese strain and, significantly, there was no virus detected in the nasal wash of the challenged animals receiving a combination of vaccine and AMPLIGEN® administered by the intranasal route while various amounts of virus were detected using the vaccine alone, AMPLIGEN® alone, intranasally, and a combination of vaccine and AMPLIGEN® administered subcutaneously.

It is desirable to raise antibodies to the avian flu virus in the nasal mucosa and other mucosa as this is the typical point of entry/infection and is believed to offer a significant preventative or mitigating benefit.

Example 2

Cross Protection Between Seasonal Influenza Vaccine and H5N1

Figure 2:
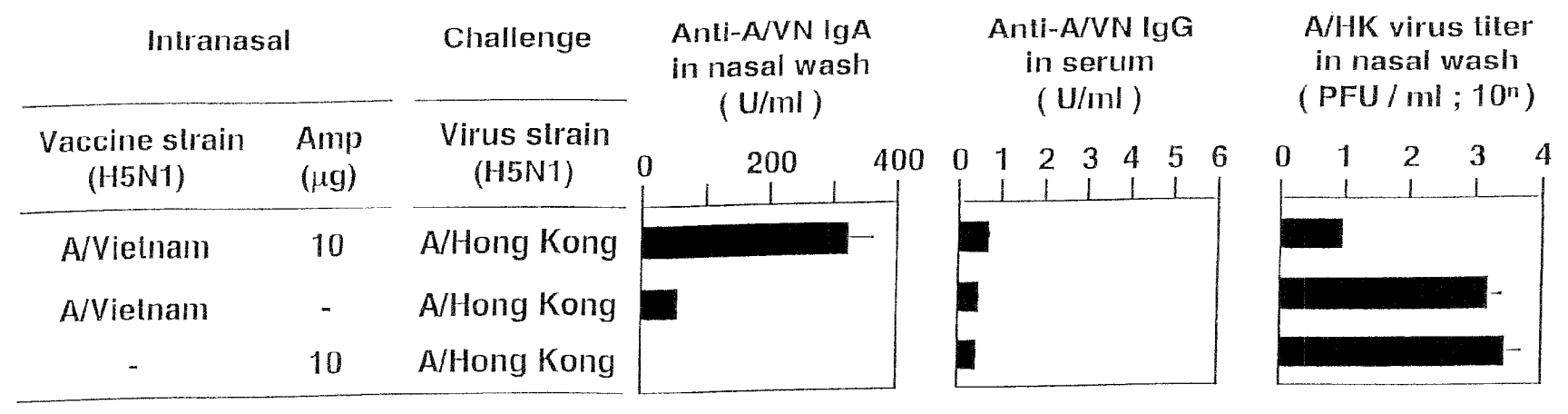

A second set of studies was completed similar to Example 1, this time initially using inactivated avian influenza virus vaccine Vietnam strain in combination with AMPLIGEN® or AMPLIGEN® alone or the vaccine alone then later challenging with the different Hong Kong strain of avian influenza virus. The results are shown in FIG. 2. The first two panels under anti-A/VN-IgA and anti-A/VN IgG were prior to challenge and the third panel was subsequent to challenge with the Hong Kong strain. Overall, beneficial results were noted in the virus titer nasal wash subsequent to challenge with the best results achieved using the combination of Vietnam strain vaccine and AMPLIGEN® and subsequent challenge with the Hong Kong strain of the virus.

These results indicate continued efficacy when the Vietnam strain vaccine-treated patients also receiving AMPLIGEN® were later challenged with the Hong Kong strain of the virus and from this it is expected that similar results will occur when the viral strains are reversed and the Hong Kong virus is used to raise the vaccine followed by subsequent challenge with the Vietnam strain.

Example 3

Viral Antigen Sparing and Augmentation

Figure 6:
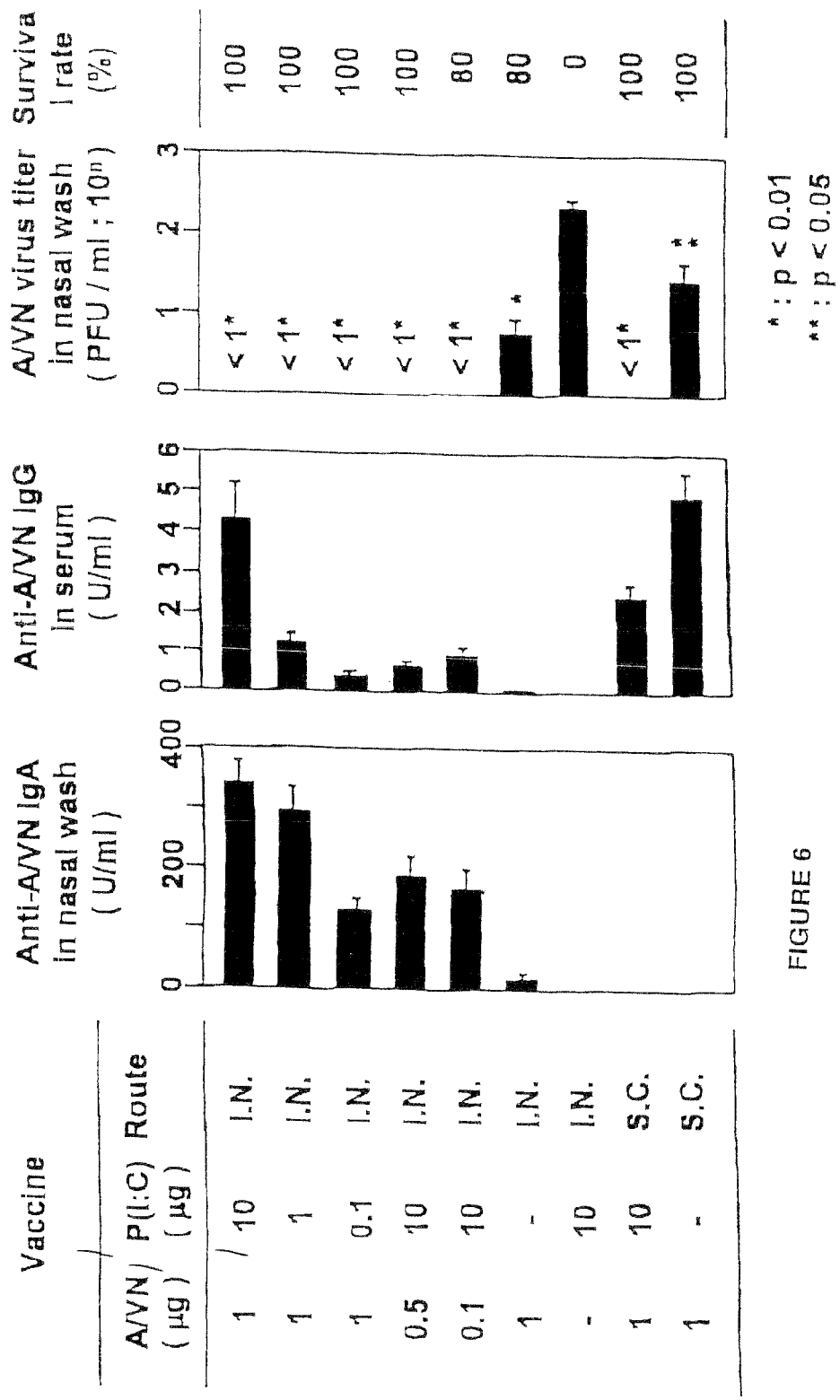
FIG. 6 is a table showing the results of Example 3.

In this example a study was made to determine how the influence of poly(I:C) on the administration of an avian influenza, Vietnam strain in animals similar to those used in Example 2. The results are presented in FIG. 6. Various doses of the avian influenza vaccine (A/VN) were employed and varying amounts of poly(I:C) were used including no A/VN and no poly(I:C) as controls. Of particular interest is a comparison between 1 µg of avian influenza vaccine and no poly(I:C) contrasted with 0.1 µg of avian influenza vaccine and 10 µg of poly(I:C). When administered intranasally in the first panel of bar graphs it will be noted that more antibodies were raised by the combination of 0.1 µg of A/VN and 10 µg of poly(I:C) compared to a tenfold larger amount of avian influenza vaccine used by itself. Of particular significance is the final panel under the heading Survival Rate where the survival rate was numerically the same, on a percentage basis, between the use of one-tenth the amount of avian influenza vaccine in combination with 10 µg poly(I:C) and 10 µg of A/VN alone (without poly(I:C)). Note also the A/VN virus titer in the nasal wash was rather insignificant for the combination of 0.1 µg A/VN and 10 µg poly(I:C) as compared to a measurable value when the avian flu vaccine was used alone. From these data one may conclude the use of poly(I:C) as an adjuvant enables one to reduce by tenfold (in this example) the amount of avian influenza vaccine necessary to achieve significant rates of survival.

Presence of the AMPLIGEN® appears to possess cross-protection ability against variant avian influenza viruses and thereby mitigate antigenic drift of the avian influenza virus.

Antigenic drift is a change in structure of a virus, such as the internal and external proteins, glycoproteins, glycolipids, etc., due to fundamental change in the genomic content of the virus particle. dsRNAs reduce the phenomenon of viral escape and cellular damage attendant thereto. Viral escape is a process by which a virus or intracellular pathogen alters its host range or indirectly alters its susceptibility of antiviral or immunological therapies.

This invention includes methods of cross-protecting animals, including humans, susceptible to avian influenza infections against viral-induced pathology secondary to both antigenic drift and shift (produced by mutations or rearrangement of the viral genetic material).

Figure 3:
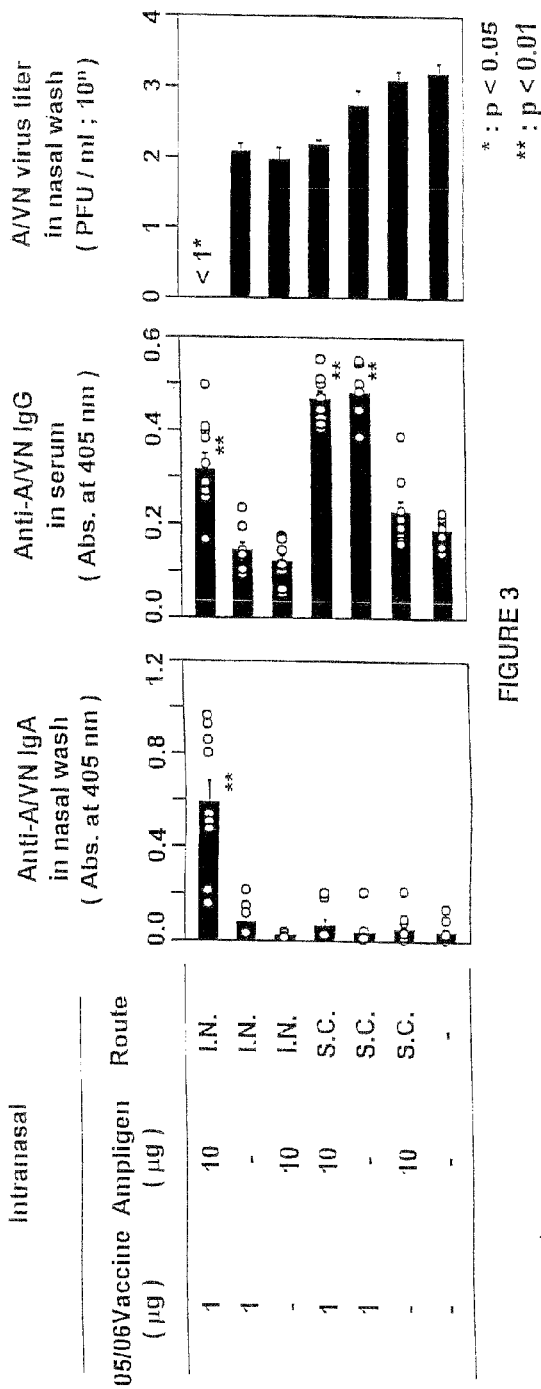
FIG. 3 is a table showing the results of Example 3 using a trivalent influenza vaccine.

In FIG. 3, seven groups of mice, five mice per group, were selected. Four of these groups were exposed to the 2005/2006 trivalent influenza vaccine either intranasally or subcutaneously. Within 21 days intranasal inoculation was repeated and within 14 days intranasal inoculation was completed again making a total of one initial inoculation and two boosters.

Two weeks after the second booster the mice were then subjected to challenge with the avian influenza VN1194 (H5N1) strain and assessed for the presence and amount of IgA anti-A/VN in a nasal wash and for IgG antibodies in serum. The results indicate that only with the presence AMPLIGEN® and administration by the intranasal route were A/VN IgA antibodies raised against the avian influenza Vietnam (VN1194) strain. While IgG antibodies were raised in the serum against the VN1194 strain from the intranasal administration there were serum antibodies raised with or without the presence of AMPLIGEN® using the SC route of administration. Virus titers for the avian flu virus were then assessed after avian influenza VN1194 (H5N1) virus challenge in nasal wash. For the subset receiving both the trivalent seasonal vaccine and AMPLIGEN® adjuvant the virus was effectively neutralized while the other groups showed measurable quantities of the A/VN virus.

Figure 4:
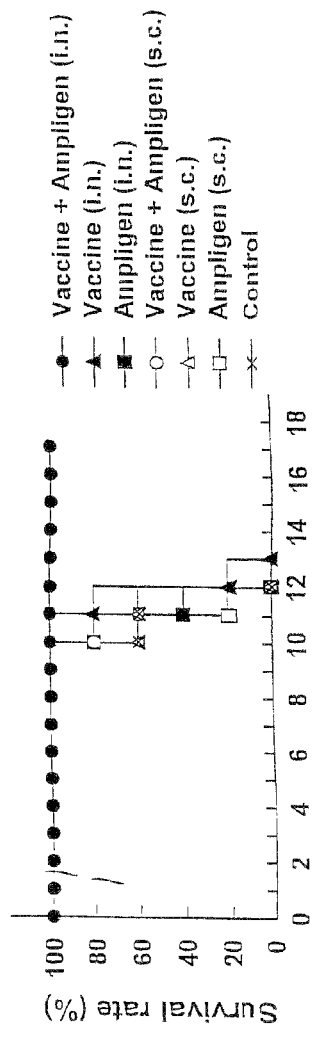
FIG. 4 is a table showing the results of Example 3 using a trivalent vaccine plus AMPLIGEN® intranasally.

FIG. 4 shows that the only group of animals to survive the challenge with VN1194 as assessed over a period of 18 days, was the group which received both the 05/06 trivalent vaccine plus the AMPLIGEN® intranasally. While antibodies were present in the blood serum they provided no effective protection against VN1194 challenge but antibodies present in the nasal mucosa were effective to prevent infection and death over the period of time measured. These findings are significant as they demonstrate in this study protection against avian influenza H5N1 strains is conferred by the use of a trivalent seasonal vaccine administered intranasally with AMPLIGEN® as a vaccine adjuvant.

Figure 5:
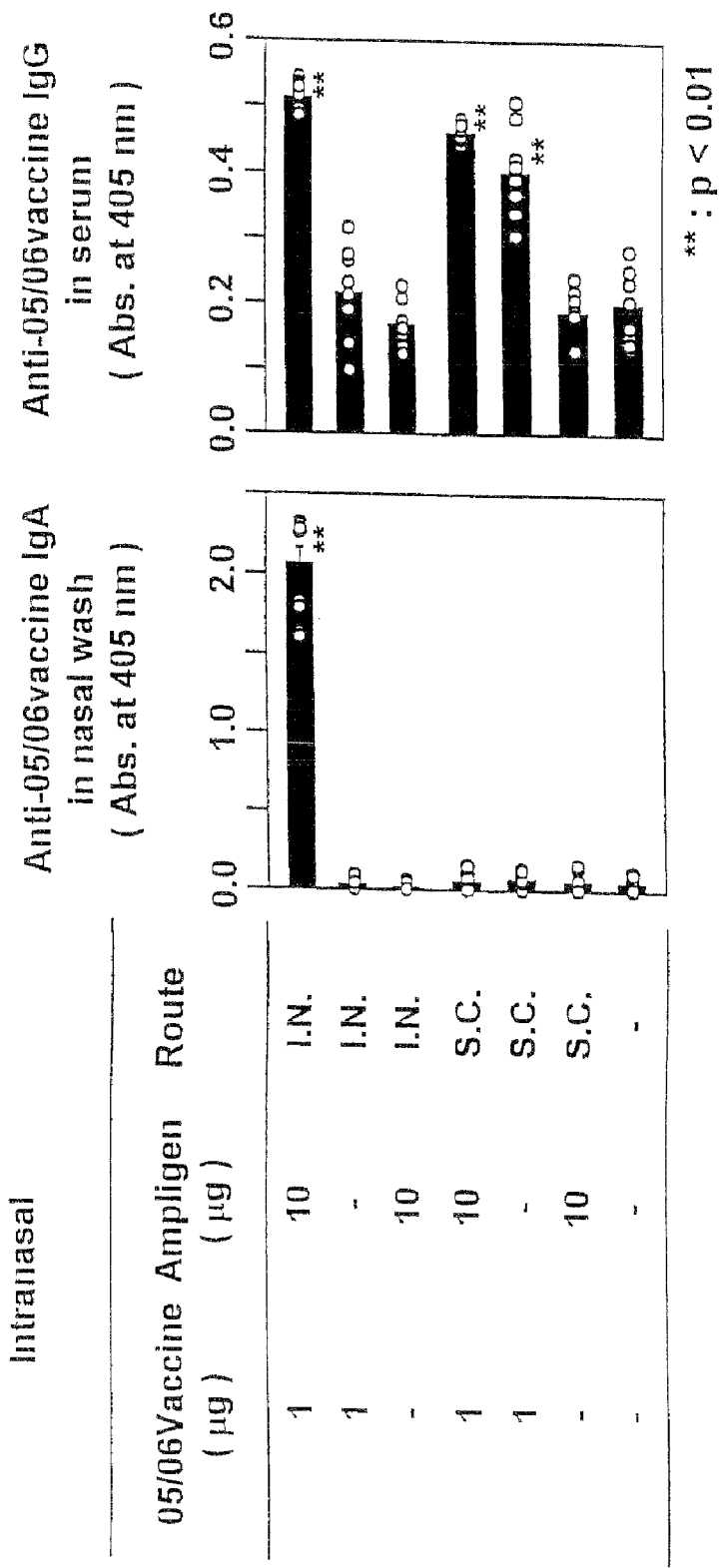
FIG. 5 is a table showing a direct cross assessment according to Example 3 of trivalent seasonal influenza vaccine and intranasally administered AMPLIGEN®.

FIG. 5 shows the direct cross assessment, again indicating the quantities and amounts of 05/06 trivalent vaccine, AMPLIGEN® and route of administration but measuring for the antibodies to be elicited against the seasonal trivalent vaccine as measured either in the nasal mucosa or blood serum. The results show antibodies against the seasonal vaccine were present in the nasal mucosa of only those animals receiving both the trivalent 05/06 seasonal vaccine and AMPLIGEN® administered by the intranasal route. Regarding the detecting of antibodies against the 05/06 trivalent vaccine in serum, all of the groups had a certain elevated "baseline" level, but a significant increase was seen both times the vaccine was used with AMPLIGEN®.

Our studies also demonstrate the presence of antibodies in blood serum does not necessarily provide an accurate indicator of protection against avian influenza and the more reliable indicator is the antibodies raised in the nasal mucosa.

Additional key cellular mechanisms induced by double-stranded RNAs to provide for more potent immune stimulating effects of influenza and other vaccines.

| Target | Activity | Result |
| --- | --- | --- |
| Epithelial cells | Activate antiviral defenses Secrete interferon. | Restricts viral replication in infected, and surrounding cells. Initiate supportive immune response. |
| Dendritic Cells | Activate DC antigen presentation, costimulatory function, and inflammatory cytokine release. | T cell activation and differentiation into T helper cells, and T killer CTL cells. |
| Macrophages | Activate phagocytosis and inflammatory cytokine release. | Increased killing and clearing of virally infected cells. |
| Mast cells | Cytokine release | Enhance recruitment and activation of immune cells at affected tissue sites. |
| Natural Killer (NK) cells | Lysis of virally infected cells, Further dendritic cell activation. | Enhance viral clearance and boost immune responses. |
| Gamma-delta T cells | Activate innate sentinel T cells in epithelial tissues. | Enhance immune responses. |
| CD4 and CD8 T cells | Augment T cell activation, differentiation, cytokine secretion, and survival | Enhance magnitude of immune responses. |

Avian influenza co-administration studies were extended to a primate model, where vaccination plus co-administered AMPLIGEN® was well tolerated and effective. In this study macaques were vaccinated with A/VN plus AMPLIGEN® (A/Vietnam (H5N1) 90 µg/500 ml, AMPLIGEN® 500 µg), for three doses, spaced 3 and 2 weeks apart. That is, an initial dose, 3 weeks later a second dose and 2 weeks later a third dose. Then the monkeys were challenged 2 weeks after the third does with high doses of A/VN (A/Vietnam (H5N1) $2.5 \times 10^5$ pfu/ 2.5 ml (lung) and A/Vietnam (H5N1) $0.5 \times 10^5$ pfu/0.5 ml nasal)) intra-tracheally and intranasally. Infected control animals developed tachypnea, coughing, weight loss, and focal consolidating pneumonia. Vaccinated animals were symptom free, and protected from disease with normal appearing pulmonary tissue.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

The invention claimed is:

1. A method of enhancing the immune response against a H5N1 avian influenza infection, the method comprising:
   (i) co-administration of a seasonal influenza vaccine and a mismatched dsRNA, or
   (ii) administration of a composition comprising a seasonal influenza vaccine and a mismatched dsRNA,
   wherein the mismatched dsRNA is $rI_n \cdot r(C_{12},U)_n$, in which n is an integer, rI is polyriboinosinic acid and $r(C_{12},U)$ is a polyribocytidylic acid sequence containing unpaired uracils,
   wherein the mismatched dsRNA acts as an adjuvant or immuno-stimulant, and
   wherein the method results in an enhanced immune response against an H5N1 avian influenza infection compared to the administration of seasonal influenza vaccine without the mismatched dsRNA.

2. The method according to claim 1 in which the mismatched dsRNA is additionally complexed with an RNA-stabilizing polymer.

3. The method according to claim 2 in which the stabilizing polymer is lysine or cellulose.

4. The method according to claim 1, part (i), wherein the seasonal influenza vaccine is administered intranasally and the mismatched dsRNA is administered intranasally.

* * * * *